United States Patent [19]

Randall

[11] 4,293,505

[45] Oct. 6, 1981

[54] PREPARATION OF β-HALOETHYLPHOSPHONIC ACIDS AND HALF ESTERS THEREOF

[76] Inventor: David I. Randall, 417 Dogwood Ter., Easton, Pa. 18042

[21] Appl. No.: 117,334

[22] Filed: Jan. 31, 1980

Related U.S. Application Data

[60] Division of Ser. No. 872,766, Oct. 30, 1969, which is a continuation-in-part of Ser. No. 628,839, Apr. 6, 1967.

[51] Int. Cl.$^3$ ............................................ C07F 9/40
[52] U.S. Cl. .............................. 260/983; 260/502.4 R; 260/961
[58] Field of Search ........................................ 260/983

[56] References Cited

U.S. PATENT DOCUMENTS 3,626,037  12/1971  Randall et al. ................. 260/983 X
3,787,486  1/1974   Randall et al. ..................... 260/983

FOREIGN PATENT DOCUMENTS 2501185  7/1976  Fed. Rep. of Germany ...... 260/983

Primary Examiner—Anton H. Sutto
Attorney, Agent, or Firm—James Magee, Jr.; Marilyn J. Maue

[57] ABSTRACT

A process for producing β-haloethylphosphonic acids, by cleaving bis(alkyl or haloalkyl) β-haloethylphosphonate with anhydrous hydrogen halide at a temperature of 140°–175° C.

10 Claims, No Drawings

PREPARATION OF β-HALOETHYLPHOSPHONIC ACIDS AND HALF ESTERS THEREOF

This is a division of Ser. No. 872,766, filed Oct. 30, 1969, which is a continuation in part of Ser. No. 628,839, filed Apr. 6, 1967.

This invention relates to the production of phosphonic acids and more particularly to a new and improved process for producing β-haloethylphosphonic acids and still more particularly to the production of β-chloroethylphosphonic acid and half esters thereof.

β-haloethylphosphonic acids are known in the art as being valuable as plant growth stimulants in the agricultural field. Thus, these compounds, particularly the chloro compound, have been used extensively as plant growth hormones for increasing crop yields of, for example, pineapples, soy beans and the like. The usefulness of these compounds is illustrated for example in the publication, Nature, Vol. 218, page 974, (1968) by Cook and Randall.

In preparation of these products, however, the processes known heretofore have not been satisfactory as they have not been able to provide a product of sufficient purity as to obviate all the toxicity effects of impurities normally contained therein. One of the most suitable procedures for the preparation of such compounds is by hydrolysis of the corresponding diester with aqueous HCl. The aqueous hydrochloric acid hydrolysis is a procedure known in the art as illustrated for example in the textbook by Kosolapoff, titled, *Organophosphorus Compounds*, John Wiley & Sons Inc., New York (1950) page 139, which indicates that esters of phosphonic acid are readily hydrolyzed by hot hydrochloric or hydrobromic acid at atmospheric pressure. To the present however, none of the published processes known for hydrolysis of the diester to the desired β-haloethylphosphonic acid has been suitable to provide the highly pure products desired.

An object of this invention is to provide a new and improved process for producing β-haloethylphosphonic acids and half esters thereof.

Another object of this invention is to provide a process for producing such acids and half esters in good yields at low cost.

Still another object of the invention is to provide a new and improved process that is particularly suitable for producing β-chloroethylphosphonic acid and its half esters.

These and other objects of the invention will be more apparent from reading the following detailed description thereof.

Attainment of the above objects is made possible by my invention which includes a process for producing β-haloethylphosphonic acid comprising introducing anhydrous HCl or HBr from an outside source into a diester stable at a temperature above 140° C. and having the formula

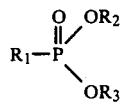
I wherein $R_1$ is β-haloethyl and $R_2$ and $R_3$ represent the same or different alkyls or haloalkyls containing no more than 6 carbon atoms, at a temperature of about 140° C. to 165° C. until a product is obtained containing about 3 to 40% of the corresponding monoester of the formula

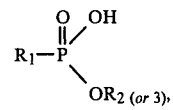
II no more than 5% of dehydrohalogenated impurities, no more than about 5% of other impurities, and the balance β-haloethylphosphonic acid or anhydride.

As only representative examples of diesters which may be cleaved in accordance with the process of the invention there may be mentioned: bis(2-chloroethyl) β-chloroethylphosphonate; bis(2-chloropropyl) β-chloroethylphosphonate; dimethyl β-bromoethylphosphonate; diethyl β-chloroethylphosphonate; ethyl isopropyl β-bromoethylphosphonate; gamma-bromopropyl n-hexyl β-chloroethylphosphonate; and the like. The chloro and bromo substituents may instead be iodo and/or fluoro. These diesters, and methods for their production, are generally known. They may be prepared for example by isomerization of the corresponding tris(alkyl and/or haloalkyl)phosphite containing at least one β-haloethyl group by heating, preferably in the presence of an inert organic diluent such as o-dichlorobenzene, cumene, xylene or the like at an elevated temperature such as about 160° C.

The claimed process involves a cleavage or displacement as distinguished from the hydrolysis reaction disclosed in the prior art, and proceeds in two steps, the first step being more readily accomplished and involving cleavage of one of the ester groups in the starting diester to produce the corresponding monoester according to the equation (using HCl in the process)

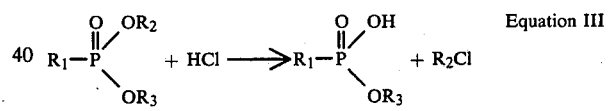
Equation III

The second step of the reaction, represented by the following equation

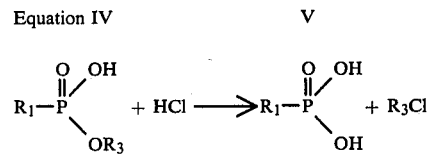
Equation IV         V is more difficult, but always results in a product substantially devoid of the precursor diester. The product usually contains small amounts of the dianhydride of the free β-haloethylphosphonic acid which is actually equivalent to the free acid since it is readily hydrolyzed thereto when the product is applied to plants from an aqueous solution, and/or by the plant itself. The reaction could be carried to completion to produce a product devoid of the monoester precursor in Equation IV, but for reasons more fully explained below, it is essential that the reaction be allowed to proceed only until a minimum of about 3% of the monoester up to a maximum of about 40% remains in the product. This monoester need not be removed when the product is employed as a plant growth regulator since it is also hydrolyzed during application thereof or by the plant, though with more difficulty than the dianhydride. If desired, the monoester can be removed from the product by extraction with a $C_{1-8}$ halohydrocarbon such as chlorobenzene, dichlorobenzene, chloroform, tetrachloroethylene, but preferably methylene chloride or ethylene dichloride.

The β-haloethylphosphonic acid products of the present invention, with or without purification, may be reacted with phosphorous pentachloride to produce β-haloethylphosphonyl dichloride, a valuable intermediate. In addition, and more important, they act as plant hormones and aqueous solutions containing them may be applied to growing plants to regulate growth characteristics thereof. The β-haloethylphosphonic acids are generally sprayed onto the plants in an amount to provide between about 0.1 lb. and about 16 lbs. of the acid per acre of plants. A variety of beneficial effects are obtained including substantially increased yields of fruits and vegetables.

In the above described use of these products in the agricultural field, and particularly with respect to food crops, it is essential that the product be devoid of undesirable impurities or adulterants. In carrying out the process of this invention, an entirely unexpected phenomenon has been found to occur, namely the tendency to produce dehydrohalogenated products (containing ethylenic or vinyl linkages); it was entirely unsuspected that dehydrohalogenation could take place in the claimed process which is carried out in the presence of anhydrous hydrogen halide, e.g. HCl or HBr, at 140°–165° C. Indeed one would predict that dehydrohalogenation would be entirely suppressed in the presence of the hydrogen halide gas at elevated temperatures. Such dehydrohalogenated products are for obvious reasons undesirable and the specified conditions of this process are accordingly essential for producing a product containing no more than 5% of such dehydrohalogenated materials.

It has been found in accordance with this invention that it is essential to keep the reaction temperature below about 165° C. to avoid excessive production of dehydrohalogenated materials. It has likewise been found that the proportion of dehydrohalogenated material in the product increases as the reaction approaches completion and the proportion of monoester in the product approaches a minimum or zero. It is accordingly also essential to allow the reaction to proceed only until a minimum of about 3% of monoester is present in the product. There is a greater tendency to form dehydrohalogenated products when $R_2$ and/or $R_3$ are haloalkyl, and in such cases, the reaction should be run only until a minimum of about 20% up to about 40% of the monoester remains in the product, whereby the production of dehydrohalogenated products is held to no more than 5%. When $R_2$ and $R_3$ are alkyl, the reaction may be permitted to run until the monoester in the product amounts to about 3 to 20%.

It will be understood that a further feature of this invention is the provision of a process for producing the monoester of formula II by Equation III above. The proportion of monoester in the product is substantially increased by stopping the reaction before the second step of Equation IV has progressed to any substantial degree, but after substantially complete disappearance of the precursor diester. In this manner, products are obtained containing over 50% of the monoester which can if desired be separated out by extraction with a halohydrocarbon as described above.

Still another feature of the invention is the provision of a process for producing the free acid of formula V from said monoester by Equation IV above.

Control of the reaction steps and the production of the desired products in accordance with the processes of this invention may be maintained by any one or a combination of the following expedients:

1. Measure the amounts of $R_2$ halide and $R_3$ halide evolved as the reaction proceeds according to Equations III and IV above.

2. React a sample of the product with an esterifying agent to convert the OH groups in the free acid (formula V above) and monoester (formula II above) to $OR_4$, $R_4$ being alkyl, e.g. methyl, different from $R_2$ and $R_3$, and analyze by VPC (vapor phase chromatography) for amounts of product containing two $OR_4$ groups derived from the free acid, amounts of product containing one $OR_4$ group derived from the said monoester, and amounts of product devoid of $OR_4$ (unreacted precursor diester of formula I above).

3. Titrate a sample of the product with NaOH for determination of the free acid content and run a chlorine (or other halogen) analysis on a sample of the same product, effective for determining amounts of free acid and monoester wherein $OR_3$ is chloroalkyl (or other haloalkyl).

4. Determine the relative disappearance from samples of the product of terminal methyl groups in the precursor diester or monoester by NMR (nuclear magnetic resonance) procedure.

Any one or a combination of the foregoing control or analytical procedures may be employed for determining the exact conditions of time and temperature and the like for producing the desired product from any particular precursor diester or monoester.

The following examples are only illustrative of various embodiments of this invention and are not to be regarded as limitative. All parts and proportions referred to herein and in the appended claims are by weight unless otherwise indicated.

EXAMPLE I 1938 grams of crude bis(2-chloroethyl) β-chloroethylphosphonate, prepared by the rearrangement of tris(2-chloroethyl) phosphite in o-dichlorobenzene, were introduced into a 3 liter 3 neck flask, equipped with stirrer, glass inlet tube and a "Y" tube, containing a thermometer which extended below the liquid surface. The other arm of the "Y" tube was attached to a down dropping bulb condenser attached to a one liter one neck distillation flask, containing a side arm which was connected to a cascade water scrubbing tower for removal of excess hydrogen chloride. The crude diester was heated, with stirring, to a temperature of 159°–160° C., at which temperature anhydrous hydrogen chloride from a pressure cylinder was introduced beneath the surface of the liquid, resulting in vigorous evolution of 1,2-dichloroethane. The addition of hydrogen chloride was continued for 6.5 hours while maintaining the same temperature. The evolution of 1,2-dichloroethane was very rapid during the first four hours. The resulting product weighted 1039 grams, had a melting point of 35°–55° C., and contained 34.6% of the mono 2-chloroethyl ester of β-chloroethylphosphonic acid, 48.4% of the free β-chloroethylphosphonic acid and 11% of its anhydride, 2.2% of dehydrochlorinated impurities, and the balance other impurities.

100 grams of the above product were extracted with 4 consecutive 100 gram portions of methylene chloride ($CH_2Cl_2$), in which the said free acid and its anhydride are substantially insoluble. About 65 grams of white crystalline material remained composed of said free acid and anhydride with about 5% of said monoester and dehydrohalogenated material.

The solvent in the combined extracts from the above 4 extractions was distilled off leaving about 35 grams of a thick syrup composed of said monoester with about 5% of said free acid and dehydrohalogenated material.

EXAMPLE II

Following the procedure of Example I, anhydrous HCl was passed through 39.8 grams (0.2 mole) of diethyl β-chloroethylphosphonate of 85–90% purity, prepared by reaction of vinyl chloride with diethylphosphite, at about 150° C. for about 16 hours and until about 70–85% of theory of ethyl chloride byproduct was collected in a trap cooled with dry ice-acetone. The viscous liquid product was subjected to vacuum pumping to constant weight, 27 grams (theoretical yield of pure β-chloroethylphosphonic acid is 28.8 grams). Analysis of the product showed:

72.9% β-chloroethylphosphonic acid
5.3% β-chloroethylphosphonic acid anhydride(bis)
5.0% mono(2-chloroethyl) ester of β-chloroethylphosphonic acid
4.0% dehydrochlorinated products This invention has been disclosed with respect to certain preferred embodiments thereof, and it will be understood that modifications and variations thereof will become obvious to workers of ordinary skill in this art and are to be included within the spirit and purview of this application and the scope of the appended claims.

I claim:

1. A process for producing β-haloethylphosphonic acid which comprises introducing anhydrous HCl or HBr from an outside source into a diester stable at a temperature above 140° C. and having the formula

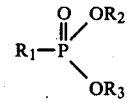

wherein $R_1$ is haloethyl and $R_2$ and $R_3$ represent alkyl or haloalkyl containing no more than 6 carbon atoms, at a temperature of about 140° C. to 165° C. until a product is obtained containing about 3 to 40% of the corresponding monoester of the formula

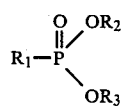

no more than 5% of dehydrohalogenated impurities, no more than about 5% of other impurities, and the balance β-haloethylphosphonic acid or anhydride.

2. A process as defined in claim 1 wherein $R_1$ is chloroethyl.

3. A process as defined in claim 2 wherein at least one of $R_2$ and $R_3$ is haloalkyl and the anhydrous HCl or HBr is introduced until the product contains about 20 to 40% of the corresponding monoester.

4. A process as defined in claim 3 wherein $R_2$ and $R_3$ are chloroethyl and anhydrous HCl is introduced into said diester.

5. A process as defined in claim 1 wherein $R_1$ is chloroethyl and $R_2$ and $R_3$ are alkyl.

6. A process as defined in claim 5 wherein the anhydrous HCl or HBr is introduced until the product contains about 3 to 20% of the corresponding monoester.

7. A process as defined in claim 6 wherein anhydrous HCl is introduced into said diester.

8. A process comprising introducing anhydrous HCl or HBr from an outside source into a diester stable at a temperature above 140° C. and having the formula

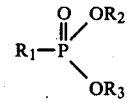

wherein $R_1$ is β-haloethyl and $R_2$ and $R_3$ represent alkyl or haloalkyl containing no more than 6 carbon atoms, at a temperature of about 140° C. to 165° C. until a product is obtained substantially devoid of said diester and containing over 50% of the corresponding monoester of the formula

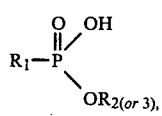

9. A process comprising introducing anhydrous HCl or HBr from an outside source into a monoester of the formula

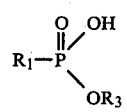

wherein $R_1$ is β-haloethyl and $R_3$ is alkyl or haloalkyl of no more than 6 carbon atoms, at a temperature of about 140° C. to 165° C. until a product is obtained containing about 3 to 40% of said monoester, no more than about 5% of other impurities, and the balance β-haloethylphosphonic acid or anhydride.

10. A process as defined in any of claim 1, 8 and 9 followed by the step of extracting said monoester from said product with a $C_{1-8}$ halohydrocarbon.

* * * * *